US00PP16177P3

(12) United States Plant Patent
Cain et al.

(10) Patent No.: US PP16,177 P3
(45) Date of Patent: Jan. 3, 2006

(54) GRAPEVINE NAMED 'SUGRATWENTYFOUR'

(50) Latin Name: *Vitis vinifera*
Varietal Denomination: Sugratwentyfour

(75) Inventors: David W. Cain, Bakersfield, CA (US); Michael J. Striem, Bakersfield, CA (US)

(73) Assignee: Sun World International, Inc., Bakersfield, CA (US)

( * ) Notice: Subject to any disclaimer, the term of this patent is extended or adjusted under 35 U.S.C. 154(b) by 150 days.

(21) Appl. No.: 10/618,357

(22) Filed: Jul. 10, 2003

(65) Prior Publication Data

US 2005/0010980 P1 Jan. 13, 2005

(51) Int. Cl.
*A01H 5/00* (2006.01)

(52) U.S. Cl. ..... Plt./207

(58) Field of Classification Search ..... Plt./207
See application file for complete search history.

(56) References Cited

U.S. PATENT DOCUMENTS

PP5,151 P 12/1983 Hahn et al. ..... Plt./47

*Primary Examiner*—Anne Marie Grunberg
(74) *Attorney, Agent, or Firm*—Knobbe, Martens, Olson & Bear, LLP

(57) ABSTRACT

A new and distinct grapevine variety characterized by medium-sized round, green-yellowish seedless grapes with mild muscat flavor and a crisp texture. The new variety is a mid-season variety, ripening before any other muscat flavored, seedless grape cultivars grown in California. The grapes of the new variety have medium sugar content and excellent eating quality.

1 Drawing Sheet

Latin name of the genus and species claimed: *Vitis vinifera.*
Variety denomination: 'Sugratwentyfour'.

BACKGROUND AND SUMMARY OF THE INVENTION

This invention relates to the discovery and asexual propagation of a new variety of grapevine as herein described and illustrated. The new variety is characterized by medium-sized, white seedless berries having a desirable distinctive muscat flavor, and a crisp juicy flesh. The grapes are round with a tough skin that is greenish yellow in color, and are of excellent eating quality. The new variety ripens midseason, before any other muscat flavored, seedless grape cultivars grown in California.

The new variety was first hybridized by David W. Cain and Michael J. Striem in Wasco, Kern County, Calif., the variety being originated by controlled hybridization and subsequent ovule culture of seed traces and abortive embryo. The seed parent is the variety 'Black Monukka' (unpatented), and the pollen parent is 'Sugrafive' (U.S. Plant Pat. No. 5,151). The parent varieties were first crossed in May 1988, with the date of first sowing being August 1988 and the date of first flowering being May, 1991. The new 'Sugratwentyfour' variety was first asexually propagated by David W. Cain in January, 1992, in Wasco, Kern County, using hardwood cuttings.

The new grapevine variety 'Sugratwentyfour' resembles its seed parent 'Black Monukka' in most characteristics. However, the new variety differs from its seed parent in having light-yellow colored grapes, while 'Black Monukka' bears black colored grapes.

The new grapevine variety 'Sugratwentyfour' resembles its pollen parent 'Sugrafive' in many characteristics such as berry color, berry firmness and berry texture. The new variety 'Sugratwentyfour' differs from its pollen parent 'Sugrafive' by having more nearly round berries than 'Sugrafive.' Further, the new variety 'Sugratwentyfour' ripens later than 'Sugrafive.'

'Sugratwentyfour' is distinguished from other commonly grown white seedless grapevine varieties such as 'Sugraeighteen', 'Sugraone', 'Perlette', and 'Thompson Seedless.'

The new grapevine variety 'Sugratwentyfour' resembles the 'Sugraeighteen' grapevine variety by its distinct muscat flavor, berry shape and color. The new grapevine variety differs from the 'Sugraeighteen' variety by having a substantially earlier ripening period—grapes of 'Sugratwentyfour' ripen about the same time as 'Sugraone' and 'Thompson Seedless' varieties. Additionally, the vine of the new variety is more vigorous and less productive (cane pruned) than 'Sugraeighteen' (spur pruned).

The new grapevine variety 'Sugratwentyfour' differs from the 'Sugraone', 'Perlette' and 'Thompson Seedless' and other commonly grown white seedless grapevine varieties by possessing a distinct and moderately mild muscat flavor somewhat similar to that of the seeded Italia grapevine varieties. It also differs from the above listed varieties by having much more nearly round berries than 'Sugraone' or 'Thompson Seedless.'

The new 'Sugratwentyfour' variety has been shown to maintain its distinguishing characteristics through successive asexual propagations by, for example, cuttings.

BRIEF DESCRIPTION OF THE FIGURE

The accompanying photographic illustration in FIG. 1 illustrates in full color a typical cluster of berries, a young shoot, and a mature leaf blade of the new grapevine. The colors are as nearly true as is reasonably possible in a color representation of this type.

DETAILED BOTANICAL DESCRIPTION OF THE INVENTION

Figure 1:
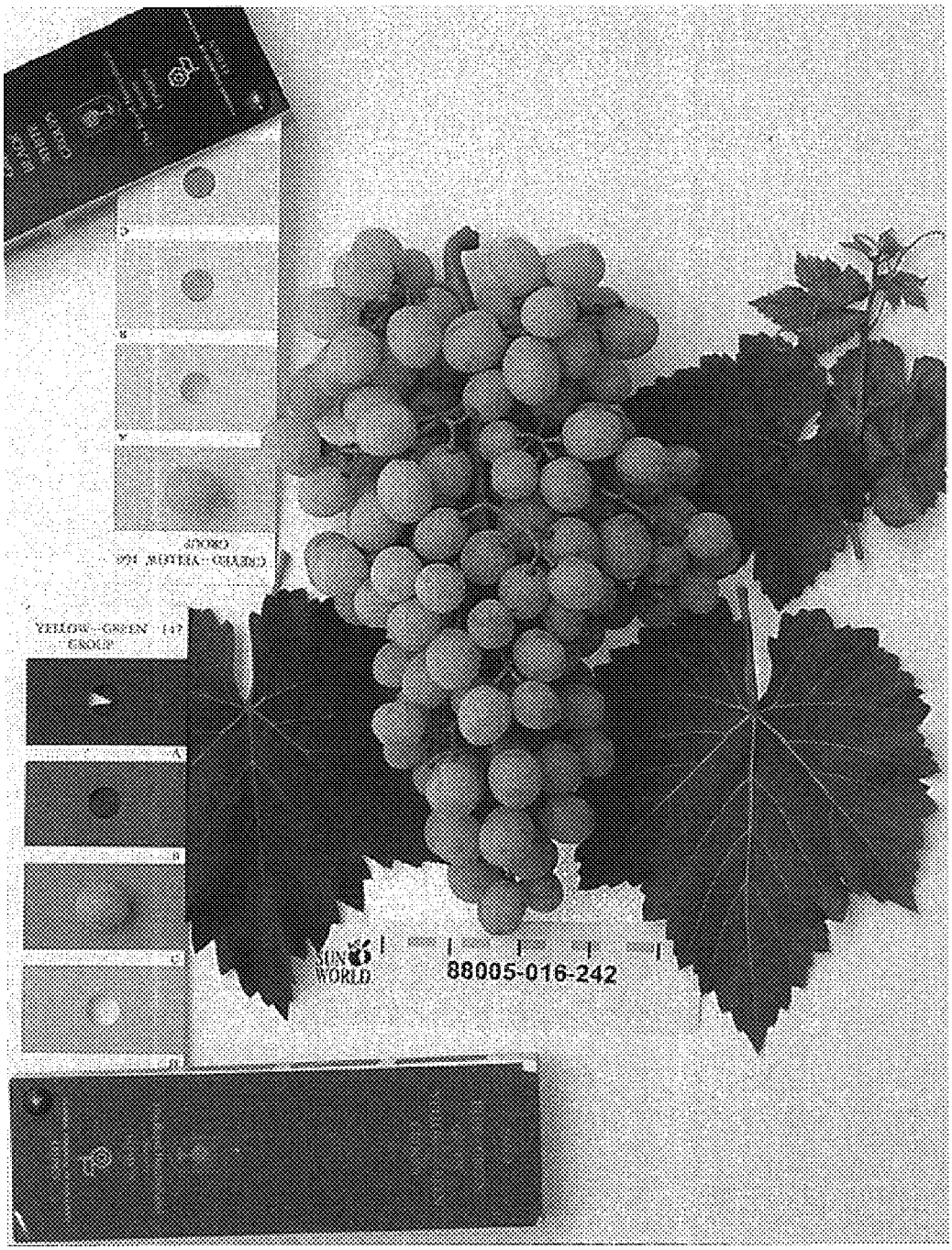

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England.

Many of the description values in this specification are based on and conform to those set forth by the International Board for Plant Genetic Resources Institute Grape Descriptors (*Vitis* spp.) of 1983 and/or 1997 which was developed in collaboration with the Office International de la Vigne et du Vin (OIV) and the International Union for the Protection of New Varieties of Plants (UPOV).

The descriptive matter which follows pertains to 'Sugratwentyfour' plants grown in the vicinity of Wasco, Kern County, Calif., during 2002, and is believed to apply to plants of the variety grown under similar conditions of soil and climate elsewhere.

VINE

General:

*Width.*—Approximately 175–200 cm.
*Height.*—Approximately 240–270 cm.
*Vigor.*—Medium — plants are moderately vigorous when pruned to six canes per vine.
*Density of foliage.*—Medium.
*Productivity.*—Medium productive — when grown on on four year old vines pruned to six canes per vine, the plant produces approximately 20–25 bunches per vine.
*Root stock.*—Own roots.

Trunk:

*Shape.*—Irregular flat elliptic to broadly elliptic.
*Surface texture.*—Medium.
*Inner bark color.*—About Greyed-orange 177B.
*Outer bark color.*—About Greyed-orange 165C (with some areas being about Grey 201B under open canopy).
*Diameter* (*at 20 cm above soil line*).—Approximately 50 mm.

SHOOTS

Young shoot:

*Form of tip.*—Half-open.
*Distribution of anthocyanin coloration of tip.*—Absent.
*Intensity of anthocyanin coloration of tip.*—Absent.
*Density of prostrate hairs on tip.*—Very sparse.
*Density of erect hairs on tip.*—Absent.
*Color.*—About Yellow-green 144B.

Woody shoot (mature canes):

*Shape of cross section.*—Circular.
*Internode length.*—Long — approximately 35.7 mm.
*Width at node.*—Approximately 14.83 mm.
*Surface.*—Ribbed.
*Main color.*—Light brown.
*Lenticels.*—Absent.
*Density of erect hairs on nodes.*—None or very sparse.
*Density of erect hairs on internodes.*—None or very sparse.
*Growth of axillary shoots.*—Weak; approximately 17.9 cm.
*Color.*—About Greyed-orange 165B to Greyed-orange 166D.

Flowering shoot:

*Vigor during flowering.*—Strong.
*Attitude during flowering on shoots which are not tied.*—Semi-erect.
*Color of dorsal side of internodes.*—About Yellow-green 144A.
*Color of ventral side of internodes.*—About Yellow-green 144A.
*Color of dorsal side of nodes.*—About Yellow-green 144A.
*Color of ventral side of nodes.*—About Yellow-green 144A.
*Density of erect hairs on nodes.*—Absent.
*Erect hairs on internode.*—Absent.
*Density of prostrate hairs on nodes.*—Absent.
*Density of prostrate hairs on internodes.*—Absent.
*Anthocyanin coloration of buds.*—Absent.

Tendrils:

*Distribution on the shoot at full flowering.*—Discontinuous.
*Thickness.*—Thick.
*Color.*—About Yellow-green 151A.
*Form.*—Bifurcated.
*Number of consecutive tendrils.*—Up to two.
*Length of tendril.*—Medium; approximately 19 cm.

LEAVES

Young leaves:

*Color of upper surface of first 4 distal unfolded leaves.*—About Green 141A.
*Average intensity of anthocyanin coloration of six distal leaves prior to flowering.*—Absent.
*Density of prostrate hairs between veins at lower surface of 4th distal unfolded leaf.*—Absent.
*Density of erect hairs between veins at lower surface of 4th distal unfolded leaf.*—Absent.
*Density of prostrate hairs on veins at lower surface of 4th distal unfolded leaf.*—Absent.
*Density of erect hairs on veins at lower surface of 4th distal unfolded leaf.*—Absent.

Mature leaves:

*Average length.*—Approximately 103 mm.
*Average width.*—Approximately 164 mm.
*Size of blade.*—Medium.
*Shape of blade.*—Pentagonal.
*Number of lobes.*—Three.
*Anthocyanin coloration of main veins on the upper side of the blade.*—Absent.
*Mature leaf profile.*—Flat.
*Blistering surface of blade upper surface.*—Absent.
*Leaf blade tip.*—Curved downwardly.
*Undulation of margin.*—Slight.
*Apex.*—Cuspidate.
*Thickness.*—Medium.
*Undulation of blade between main and lateral veins.*—Absent.
*Shape of teeth.*—Mixture of both sides straight and both sides convex.
*Length of teeth.*—Short.

*Ratio length/width of teeth.*—Small.
*General shape of petiole sinus.*—Half-open.
*Tooth at petiole sinus.*—Absent.
*Petiole sinus limited by veins.*—Absent.
*Shape of upper lateral sinus.*—Open.
*Depth of upper lateral sinus.*—Shallow.
*Density of prostrate hairs between veins on lower surface of blade.*—Absent.
*Density of erect hairs between veins on lower surface of blade.*—Absent.
*Density of prostrate hairs on main veins on lower surface of blade.*—None or very sparse.
*Density of erect hairs on main veins on lower surface of blade.*—None or very sparse.
*Density of prostrate hairs on main veins on upper surface of blade.*—Absent.
*Autumn coloration of leaves.*—About Yellow-green 153B.

Upper surface:
*Color.*—About Yellow-green 147A.
*Surface texture.*—Smooth.
*Surface appearance.*—Semi-glossy.
*Goffering of blade.*—Absent.

Lower surface:
*Color.*—About Yellow-green 146A.
*Anthocyanin coloration of main veins on lower leaf surface.*—Absent.
*Glossiness.*—Weak.
*Pubescence.*—Absent.
*Surface texture.*—Wrinkled.
*Surface appearance.*—Dull.

Petiole:
*Length of petiole.*—Medium; approximately 9.5 cm.
*Length of petiole compared to middle vein.*—Slightly shorter.
*Density of prostrate hairs on petiole.*—Absent.
*Density of erect hairs on petiole.*—Absent.
*Shape of base of petiole sinus.*—U-shaped.

Buds:
*Shape.*—Slightly pointed.
*Size.*—Medium; approximately 4 by 6 mm.
*Position.*—Slightly held out.
*Cane bud fruitfulness.*—Basal most fruitful.
*Time of bud burst.*—Early — Mar. 18, 2002.

FLOWERS

General:
*Flower sex.*—Hermaphrodite.
*Length of first inflorescence.*—Medium.
*Position of first flowering node.*—Second node.
*Number of inflorescences per shoot.*—Approximately 1.1 to 2.
*Date of full bloom.*—May 11, 2002.
*Time of bloom.*—Early (as compared to similar varieties growing in the same region.).
*Size (diameter of fully open flower).*—Approximately 4.5 mm.
*Color.*—About Yellow-green 145B.

FRUIT

General:
*Ripening period.*—Medium — approximately 0 days ahead of Thompson Seedless variety.
*Use.*—Fresh market.
*Storage quality.*—Medium — berry stays firm and crunchy but tends to develop brown rubbing marks; slight drying of stem and rachis, no shatter, some reduction in flavor, no shriveling, no rot.
*Resistance.*—Neither resistance nor susceptibility to diseases or pests has been observed in this variety.
*Shipping quality.*—Medium — some sensitivity to bruising and rubbing.
*Date of first harvest.*—Jul. 15, 2002.
*Solids-sugar.*—Medium — approximately 18%.
*Refractometer test.*—Approximately 18.0.
*Acid.*—Medium — approximately 5.04 g/liter.
*Juice pH.*—Approximately 3.9.

Cluster:
*Bunch size (peduncle excluded).*—Medium.
*Bunch length (peduncle excluded).*—Intermediate — approximately 19.4 cm.
*Bunch width.*—Approximately 16.1 cm.
*Bunch weight.*—Low — approximately 561 g.
*Bunch density.*—Loose.
*Number of berries.*—Approximately 152.
*Form.*—Cylindrical.

Peduncle:
*Length of peduncle.*—Short — approximately 4.07 cm.
*Lignification of peduncle.*—Weak.
*Color.*—About Yellow-green 146B.

Berry:
*Size.*—Medium.
*Uniformity of size.*—Variable.
*Berry weight.*—Low — approximately 3.68 g.
*Shape.*—Round.
*Presence of seeds.*—Rudimentary — approximately 0.6 mg.
*Cross section.*—Circular.
*Dimensions.*—Approximately 198 mm longitudinal axis by approximately 168 mm horizontal axis.
*Skin color (without bloom).*—About Greyed-yellow 160A.
*Coloration of flesh.*—Transparent greenish.
*Juiciness of flesh.*—Slightly juicy.
*Flesh color.*—About Greyed-yellow 161A.
*Berry firmness.*—Medium.
*Particular flavor.*—Muscat.
*Bloom (cuticular wax).*—Very weak.
*Pedicel length.*—Approximately 7.80 mm.
*Berry separation from pedicel.*—Easy.
*Visibility of hilum.*—Slightly clear.

Skin:
*Thickness.*—Medium.
*Texture.*—Smooth and moderately tough.
*Reticulation.*—Absent.
*Roughness.*—Absent.
*Tenacity.*—Free.

What is claimed is:

1. A new and distinct variety of grapevine as herein illustrated and described.

* * * * *